(12) United States Patent
Lezdey et al.

(10) Patent No.: US 6,428,791 B1
(45) Date of Patent: Aug. 6, 2002

(54) LUBRICATION COMPOSITION

(75) Inventors: John Lezdey, Voorhees, NJ (US); Jarett Lezdey, Indian Rock Beach, FL (US)

(73) Assignee: Alphamed Pharmace Vticals, Corp, Clearwater, FL (US)

( * ) Notice: Subject to any disclaimer, the term of this patent is extended or adjusted under 35 U.S.C. 154(b) by 0 days.

(21) Appl. No.: 09/290,759

(22) Filed: Apr. 13, 1999

(51) Int. Cl.[7] ..................... A61K 35/78; A61K 39/385
(52) U.S. Cl. .................... 424/195.1; 514/461; 514/465
(58) Field of Search ................ 424/195.1; 514/461, 514/465

(56) References Cited

U.S. PATENT DOCUMENTS

| | | | | |
|---|---|---|---|---|
| 5,718,317 A | * | 2/1998 | See | 424/450 |
| 5,730,987 A | * | 3/1998 | Omar | 424/195.1 |
| 5,853,755 A | * | 12/1998 | Foldvari | 424/450 |
| 5,874,437 A | * | 2/1999 | Garvey et al. | 514/258 |
| 5,906,987 A | * | 5/1999 | Chwalisz et al. | 514/177 |
| 5,922,332 A | * | 7/1999 | Fossel | 424/401 |
| 6,039,951 A | * | 3/2000 | Rjeldbak | 424/195.1 |

* cited by examiner

*Primary Examiner*—Theodore J. Criares
(74) *Attorney, Agent, or Firm*—John Lezdey

(57) ABSTRACT

A lubricating composition for use in mucosal areas is provided to enhance sexual performance. The composition contains combination of a compound which enhances blood circulation to body parts and/or increase nitrous oxide levels at the site of administration together with a compound which can generate heat without any substantial irritation or create the feel of heat in a lubrication base. Preferably, the composition is homeopatic.

9 Claims, No Drawings

LUBRICATION COMPOSITION

FIELD OF THE INVENTION

The present invention relates to a lubricant which can be used in the mucosal areas of the human body. More particularly, there is provided a lubricating composition which can be utilized to enhance sexual activity and sexual performance in individuals.

BACKGROUND OF THE INVENTION

Topical compositions containing compounds which elevate nitrous oxide are known to enhance blood circulation which can provide males with enhanced sexual activities. Compounds such as arginine, and amino acid compounds containing arginine groups have been found to elevate nitrous oxide activity in the body.

There are additionally homeopathic compounds which can improve circulation to the body parts applied. However, some of the compounds work by way of irritation which cannot be used in the genitalia area. Compounds such as capacsin have been used but result in major irritation, even when anti-irritants are utilized.

Viagara®, which is an orally administered medicament that enhances sexual performance has numerous side effects and cannot be safely utilized over a long period of time. It is therefore advantageous to provide a topically administered composition that can produce the same results as Viagara without side effects or irritation.

It would also be advantageous to incorporate in the compositions compounds which inhibit sexually transmitted diseases (STD).

The pH of a healthy vagina is mildly acidic (pH 3.5-4.5) and this acidity is thought to be generated by the production of lactic acid by lactobacilli, which form a major component of the healthy vaginal flora. Together with other factors, this acid pH is widely recognized to prevent overgrowth of undesirable endogenous microbes (Candida, harmful anaerobes, and bacteria that may cause urinary tract infections) and encourages the continued dominance of lactobacilli which, in addition to mild acidity, provides other protective mechanisms such as production of hydrogen peroxide.

It is also known that sperm are inactivated by the mild acidity of the healthy vagina, and acid substances have been used as home made vaginal contraceptives for centuries. More recently it has been recognized that many sexually transmitted disease pathogens and most or all enveloped STD viruses (Kempf 1991, Martin 1985) including herpes simplex virus, cytomegalovirus, and human immunodeficiency virus, are also inhibited or inactivated by mild acidic pH. However, semen contains a potent alkaline buffering capacity that neutralizes the vaginal acidity for a period of many hours after intercourse. This alkaline buffering capacity enables sperm to swim from the vagina into the cervix and upper genital trace.

Unfortunately, STD pathogens in genital secretions can also exploit this period of neutral vaginal pH, since it allows time for them to reach and infect their target cells. If this semen-induced neutralization of vaginal acidity could be promptly and reliably overcome, both contraception and STD prevention could be achieved by a method that closely mimics the normal psychological state of the vagina.

In addition, the elevated pH also allows certain strains of *Staphylococcus aureus* to produce shock toxin I, whereas production of this toxin is completely inhibited at acidic pH 5.0 (Schlievert 1983). Thus, loss of protective acidity may result in staphylococcal toxic shock syndrome, candida vaginitis, bacterial vaginosis, or urinary tract infection.

SUMMARY OF THE INVENTION

The present invention relates to a lubricating composition for topical use in mucosal areas which can enhance sexual performance. The compositions of the invention comprise the combination of a compound which can either enhance blood circulation to body parts and/or increase the nitrous oxide level at the site of administration, together with a compound which can generate heat without any substantial irritation or create the feel of heat.

Preferably, there is provided homeopathic compounds which can through topical application increase blood circulation and/or increase nitrous oxide together with a heat producing compound or a compound which creates a sensation of heat in a lubrication form.

Advantageously, the heat producing compounds are phytosphinosines or sphinogomyelins.

It is, therefore, an object of the invention to provide a composition that can be used to enhance sexual activity and sexual performance.

It is another object of the invention to provide a composition which can increase blood circulation and/or nitrous oxide at the site of administration, together with heat, at the area of application.

It is yet another object of the invention to provide a homeopathic composition which can be used to increase blood circulation and/or nitrous oxide together with heat, to the areas of application.

It is a further object of the invention to provide a method for enhancing sexual activity and performance by means of a composition that can be applied to the body parts.

The compositions can be applied to external genitalia as well as internal mucosal surfaces to reduce microtrauma resulting from inadequate lubrication and will prevent transmission of viable STD pathogens.

DESCRIPTION OF THE PREFERRED EMBODIMENTS

The compositions according to the invention may be presented in all forms normally used for topical application, in particular in the form of aqueous, aqueous-alcoholic or, oily solutions, or dispersions of the lotion or serum type, or anhydrous or lipophilic gels, or emulsions of liquid or semi-solid consistency of the milk type, obtained by dispersing a fatty phase in an aqueous phase (O/vv) or vice versa (VV/o), or of suspensions or emulsions of soft, semi-solid consistency of the cream or gel type, or alternatively of microemulsions, of microcapsules, of microparticles or of vesicular dispersions to the ionic and/or nonionic type. These compositions are prepared according to standard methods.

They may also be used in the form of aqueous, aqueous-alcoholic solutions, or in the form of creams, gels, emulsions or foams.

The amounts of the different constituents of the compositions according to the invention are those traditionally used in the pharmaceutical field.

When the composition of the invention is an emulsion, the proportion of the fatty phase can range from 5% to 80% by weight and preferably from 5% to 50% by weight, relative to the total weight of the composition. The oils, emulsifiers and coemulsifiers used in the composition in emulsion form are chosen from those traditionally used in the cosmetics. The emulsifier and the coemulsifier are present in the composition in a proportion ranging from 0.3% to 30% by weight, and preferably 0.5 to 30% or, better still, from 0.5 to 20%, by weight, relative to the total weight of the composition. The emulsion can, in addition, contain lipid vesicles.

When the compositions of the invention is an oily gel or solution, the fatty phase can represent more than 90% of the total weight of the composition.

In a known manner, the composition of the invention may also contain adjuvants which are customary in the pharmaceutical field, such as hydrophilic or lipophilic gelling agents, hydrophilic or lipophilic active agents, preservatives, antioxidants, solvents, perfumes and fillers. The amounts of these different adjuvants are those traditionally used in the pharmaceutical or dermatological field, and are, for example, from 0.01% to 10% of the total weight of the composition. Those adjuvants, depending on their nature, may be introduced into the fatty phase, into the aqueous phase and/or into lipid spherules.

As oils which can be used in the invention, mineral oils (liquid paraffin), vegetable oils (liquid fraction of sheat butter, sunflower oil), animal oils (perhydrosquatene), synthetic oils (Purcellin oil), silicone oils (cyclomethicone) and fluorinated oils (perfluoro polyethers) may be mentioned.

Fatty alcohols, fatty acids (stearic acid) and waxes (paraffin, carnauba, beeswax) may also be used as fatty substances.

As emulsifiers which can be used in the invention, glycerol stearate, polysorbate 60 and the PEG-6/PEG-32/glycol stearate mixture sold under the name of Tefose® 63 by the company Gattefosse may be mentioned as examples.

As hydrophilic gelling agents, carboxyvinyl polymers (carbomer), acrylic copolymers such as acrylate/alkylacrylate copolymers, polyacrylamides, polysaccharides such as hydroxypropylcellulose, clays and natural gums may be mentioned.

Lipophilic gelling agents, clays such as bentones, metal salts of fatty acids such as aluminum stearates and hydrophobic silica, or alternatively ethylcellulose and polyethylene may be mentioned.

Natural gums which may be used includes xantham gum, alginates and gelation. As hydrophilic active agents, proteins or protein hydrolysates, amino acids, polyols, urea, allantonin, sugars and sugar derivatives, water-soluble vitamins, starch and plant extracts, in particular those of the Aloe vera may be used.

As lipophilic active, agents, retinol (vitamin A) and its derivatives, tocopherol (vitamin E) and its derivatives, essential fatty acids, ceramides and essential oils may be used. These agents add extra moisturizing or skin softening features when utilized.

The compositions of the invention may include plant or herbal extracts which reduce irritation. For example, there may be utilized extracts of Paraguay tea, Kola and Guarana, which provide a source of methylxanthines, saponius, tannins, and glycosides that have been shown to be anti-inflammatory and can be used to treat irritations. The extract of Paraguay tea is known as "Mate extract" and is described in the "International Cosmetic Ingredient Dictionary", 5th Edition. Mate extract is commercially available in combination with extracts of Kola and Guarana, which is sold by Cosmetic Ingredient Resources of Stamford, Conn. under the trademark "QUENCHT".

Each of mate extract, serine protease inhibitor and aloe vera extract are known to provide anti-inflammatory activity. The anti-elastase and anti-tryptase activity of the protease inhibitor has been shown to provide a synergistic effect in treating skin inflammations. These components can be utilized to reduce irritation when an anti-viral is incorporated.

A surfactant can be included in the composition so as to provide deeper penetration of the ingredients. Many surfactants are also antimicrobial agents, for example, nonoxynol-9 and octoxynol-9. Generally about 0.05 to 2.0% by weight surfactant can be used.

The compounds which create heat or the sensation of heat include balm oil, nettle, capsicum extract, esters of nicotinic acid, nicotinyl alcohols, phytosphinosines, sphinogomyelins, and ginger. Ginger provides both heat and aids in circulation.

The compounds which promote or stimulate local blood circulation include the extractive mixtures from connective tissues of animal organs, known as "trichosaccharides", Yohimbe, sasparilla, extract from horny goat weed, Arnica Montana, elder, primrose oil, niacin L-ornithate, agaricus, Hamamelis, saw palmetto, rosemary, and the like.

Prostaglandins have been considered as being aids for treating impotency. However, it is advantageous to utilize extracts or plant products which induce prostaglandin production. Among such components there are primrose oil, flax oil and crocetin.

The amount of the heat producing, stimulating or prostoglandin producing compounds which can be used is about 0.05 to 5% by weight, preferably, about 0.5 to 2.0% of each. Most preferably mixtures are utilized because of the different body chemistry of individuals.

A preferred lubricating base is HISPAGEL a glycol-free glycerine clarthrate which is generally described as glycerine polyacrylate which is sold by Centerchem Inc of Stanford, Conn. Generally, up to about 20% by weight of the composition comprises HISPAGEL. It can be used in combination with other gellants such as Carbopols, cellulose derivatives, clays and the like.

The preferred natural gums which can be used amounts up to about 5% by weight include xantham gum, alginates and gelatin.

The preferred synthetic polymers which can be used include Carbopol, polyacrylic acid, polymethacrylic acid, hydroxyethyl, methacrylate, polyacrylamide, polyvinyl pyrrolidone and polyvinyl alcohol.

The nitrous oxide producing or elevating compounds are preferably amino acid compounds such as L-arginine, arginine containing compounds such as found in Ajinomoto, a product of Japan. The amount of the nitrous oxide producing compound is generally about 0.5% to 5.0% by weight.

The following examples illustrating the compositions of the invention are not intended to limit the scope of the invention. The amounts indicated are by weight percent unless otherwise noted.

EXAMPLE 1

Preparation of a gel.

| Ingredients | % W/W |
|---|---|
| Phytosphingosine | 5.0 |
| Primrose oil | 3.0 |
| Arginine base (10% solution) (Ajinomoto) | 5.0 |
| Carbopol 940 | 0.4 |
| Butylene glycol | 6.5 |
| Quench | 3.0 |
| Chamomile glycolic extract | 3.0 |
| Balm oil | 0.5 |
| Preservative | 0.1 |
| Fragrance | 0.1 |
| Deionized water | q.s. 100% |

To 20 ml of water with stirring is added the Carbopol 940. The mixture is stirred until hydration is complete and then butylene glycol is added. The arginine base is then added to the mixture. The remaining ingredients are mixed together and added to the first mixture. The mixing is continued until uniform.

EXAMPLE 2

A lubricant is prepared by admixing the following ingredients.

| Ingredient | Wt % |
|---|---|
| Hispagel | 20.0 |
| L-arginine | 1.0 |
| Flax Oil | 1.0 |
| Carbopol 940 | 0.4 |
| Butylene Glycol | 6.0 |
| Ginger | 0.1 |
| Ceramide III | 0.5 |
| Saffron | 0.2 |
| Yohimbe | 0.1 |
| Deionized Water | q.s. 100% |

EXAMPLE 3

A lubricating gel is prepared by admixing the following ingredients:

| | Ingredient | Wt % |
|---|---|---|
| 1. | Propylene Glycol | 43.00 |
| 2. | Polyacrylic acid | 2.10 |
| 3. | Dipropylene Glycol | 16.00 |

-continued

| | Ingredient | Wt % |
|---|---|---|
| 4. | Xanthan Gum | 0.15 |
| 5. | Ethoxydiglycol | 15.00 |
| 6. | Dimethylisosorbide | 10.00 |
| 7. | Ascorbic Acid | 2.00 |
| 8. | Chloroxylenol | 0.20 |
| 9. | Linoleamidopropyl PG-diammonium chloride phosphate | 1.50 |
| 10. | Glycereth 4.5 Lactate | 2.00 |
| 11. | Yohimbe | 2.00 |
| 12. | Ceramide II | 2.00 |
| 13. | Octoxynol-9 | 0.50 |
| 14. | Primrose Oil | 2.00 |
| 15. | Cocamidopropyl PG-dimon chloride phosphate | 1.00 |
| 16. | Water | 6.00 |
| 17. | Ginger | 0.44 |

Ingredients 1 and 2 are mixed to disperse and form a gel. About 80% of ingredient 3 is mixed with ingredient 4, added to the gel and slightly heated with admixture. the balance of 3 is mixed with ingredients 5–17 and added to the gel at 38 degrees C. After mixing, the pH is adjusted to about 4 and then the gel is brought to room temperature.

EXAMPLE 4

A lubricant is prepared by admixing the following ingredients:

| Ingredient | Wt % |
|---|---|
| HISPAGEL 200 | 15.00 |
| Propylene Glycol Stearate | 9.50 |
| Isocetyl alcohol | 5.00 |
| PEG-100 Steearate | 1.20 |
| Hyaluronic acid | 2.00 |
| Methyl paraben | 0.20 |
| Propylene glycol | 13.10 |
| Balm Oil | 0.50 |
| Sorbitan palmitate | 0.60 |
| Octoxynol-9 | 6.00 |
| Mate extract | 0.50 |
| Yohimbe | 0.50 |
| Water | q.s. 100% |

What is claimed is:

1. A lubricating composition for topical use on mucosal parts of an individual which comprises;

a) about 0.05 to 5% by weight of at least one compound derived from a plant or herb which can enhance circulation of blood to the body part at the site of application;

b) about 0.05 to 5% by weight of at least one compound derived from a plant or herb which provides heat or the sensation of heat to the body part at the site of application, c) about 0.5 to 5% by weight of L-arginine, and the remainder being a lubricating base.

2. The composition of claim 1 wherein said compound of part a) is comprises vegetal extracts.

3. The composition of claim 1 wherein said heat producing compound is selected from the group consisting of capsacin and ginger.

4. The compositon of claim 1 including a plant or herbal compound which promotes prostaglandins.

5. The composition of claim 4 wherein said prostaglandin promoting compound is primrose oil or flax seed oil.

6. The composition of claim 1 including yohimbe.

7. The composition of claim 1 including an aphrodisiac selected from the group consisting of diamiana saffron, Turneia aphrodisiaca, Irish moss, and fake unicorn root.

8. The composition of claim 1 including an extract of primrose oil or flaxseed.

9. In a condom having a lubricating composition, the improvement which comprises said lubricating composition containing about 0.5 to 5% of an extract and or spice derived from ginger plant which provides heat or the sensation of heat to the body part at the site of application.

* * * * *